United States Patent [19]
Wuchinich

[11] Patent Number: 5,334,183
[45] Date of Patent: Aug. 2, 1994

[54] ENDOSCOPIC ELECTROSURGICAL APPARATUS

[75] Inventor: David G. Wuchinich, New York, N.Y.

[73] Assignee: Valleylab, Inc., Boulder, Colo.

[21] Appl. No.: 866,953

[22] Filed: Apr. 9, 1992

Related U.S. Application Data

[60] Continuation of Ser. No. 329,747, Mar. 28, 1989, abandoned, which is a continuation-in-part of Ser. No. 133,711, Dec. 16, 1987, Pat. No. 4,922,902, which is a division of Ser. No. 20,266, Feb. 27, 1987, Pat. No. 4,750,488, and a continuation of Ser. No. 865,240, May 19, 1986, Pat. No. 4,750,902, which is a continuation-in-part of Ser. No. 770,342, Aug. 23, 1985, abandoned.

[51] Int. Cl.$^5$ ............................................ A61B 17/36
[52] U.S. Cl. ................................. 606/46; 606/34; 606/42; 606/16; 606/22; 606/27; 128/4
[58] Field of Search ............................. 128/4–6, 128/395, 397, 398; 606/2–19, 32–52; 604/19–23, 27, 28, 35, 43–45; 307/2, 6, 23, 27, 72, 73

[56] References Cited

U.S. PATENT DOCUMENTS

| | | | |
|---|---|---|---|
| Re. 30,536 | 3/1981 | Perdreaux, Jr. | 433/86 |
| 2,227,727 | 1/1941 | Leggiadro | 128/328 |
| 2,514,080 | 7/1950 | Mason | 171/327 |
| 2,714,890 | 8/1955 | Vang | 128/305 |
| 2,723,386 | 11/1955 | Camp | 340/111 |
| 2,845,072 | 7/1958 | Shafer | 128/303.14 |
| 2,874,470 | 2/1954 | Richards | 32/58 |
| 2,990,616 | 7/1961 | Balamuth et al. | 32/26 |
| 3,027,690 | 4/1962 | Roney | 51/59 |
| 3,065,749 | 11/1962 | Brass | 128/224 |
| 3,075,288 | 1/1963 | Balamuth et al. | 32/58 |
| 3,076,904 | 2/1963 | Kleesattel et al. | 310/26 |
| 3,086,288 | 4/1963 | Balamuth et al. | 30/272 |
| 3,089,790 | 5/1963 | Balamuth et al. | 134/1 |
| 3,109,426 | 11/1963 | Noonan et al. | 128/240 |
| 3,113,225 | 12/1963 | Kleesattel | 310/26 |
| 3,133,351 | 5/1964 | Von Seggern | 32/26 |
| 3,149,633 | 9/1964 | Zingale | 128/303.15 |
| 3,156,826 | 11/1964 | Matschler | 307/2 |
| 3,166,840 | 1/1965 | Bancroft et al. | 29/470 |
| 3,213,537 | 10/1965 | Bulamuth et al. | 32/28 |
| 3,352,303 | 11/1967 | Delaney | 128/24 AA |
| 3,368,280 | 2/1968 | Friedmath et al. | 32/58 |
| 3,375,583 | 4/1968 | Blank et al. | 32/26 |
| 3,380,446 | 4/1968 | Martin | 128/24 |
| 3,433,226 | 3/1969 | Boyd | 128/305 |
| 3,526,219 | 9/1970 | Balamuth | 128/2 |
| 3,546,498 | 12/1970 | McMaster et al. | 310/8.2 |
| 3,565,062 | 2/1971 | Kuris | 128/24 |
| 3,589,363 | 6/1971 | Banko | 128/276 |
| 3,636,947 | 1/1972 | Balamath | 128/66 |
| 3,693,613 | 9/1972 | Kelman | 128/24 A |
| 3,732,858 | 5/1973 | Banko | 604/22 |

(List continued on next page.)

FOREIGN PATENT DOCUMENTS

| | | |
|---|---|---|
| 2428714 | 9/1975 | Fed. Rep. of Germany ...... 128/752 |
| 1429637 | 1/1966 | France . |
| 2513109 | 3/1983 | France .............................. 606/2 |
| 415949 | 6/1966 | Switzerland . |
| 790277 | 2/1958 | United Kingdom . |

OTHER PUBLICATIONS

Von Ardenne et al., "Ultrasonic Insertion of Small-gauge Wire Probes and Hollow Needles in Living Organisms", 1960.

(List continued on next page.)

Primary Examiner—David M. Shay
Attorney, Agent, or Firm—Pennie & Edmonds

[57] ABSTRACT

This invention relates to a surgical apparatus having four general embodiments: (1) the use of an ultrasonic vibrator and a radio frequency generator to simultaneously cut and cauterize tissue, (2) the use of an ultrasonic vibrator to cut tissue coupled with the independent use of a radio frequency generator to cut tissue, (3) the exclusive use of a radio frequency generator to cut and cauterize tissue, and (4) the use of a laser to fulgerate tissue. An aspiration system is preferably combined with these embodiments to facilitate surgery and biopsy.

26 Claims, 12 Drawing Sheets

U.S. PATENT DOCUMENTS

| | | | |
|---|---|---|---|
| 3,805,787 | 4/1974 | Banko | 128/276 |
| 3,823,717 | 7/1974 | Pohlman et al. | 128/305 |
| 3,863,624 | 2/1975 | Gram | 128/758 |
| 3,902,495 | 9/1975 | Weiss et al. | 128/276 |
| 3,941,122 | 3/1976 | Jones | 128/24 A |
| 3,945,375 | 3/1976 | Banko | 128/6 |
| 3,956,826 | 5/1976 | Perdreaux, Jr. | 32/58 |
| 4,016,882 | 4/1977 | Broadwin et al. | 128/305 |
| 4,041,947 | 8/1977 | Weiss et al. | 128/276 |
| 4,063,557 | 12/1977 | Wuchinich et al. | 128/276 |
| 4,136,700 | 1/1979 | Broadwin et al. | 128/305 |
| 4,146,019 | 3/1979 | Bass et al. | 128/6 |
| 4,184,510 | 1/1980 | Murry et al. | 604/20 |
| 4,223,676 | 9/1980 | Wuchinich et al. | 128/276 |
| 4,362,971 | 12/1982 | Sloan, Jr. | 307/73 |
| 4,425,115 | 6/1984 | Wuchinich | 604/22 |
| 4,493,694 | 1/1985 | Wuchinich | 604/22 |
| 4,496,342 | 1/1985 | Banko | 604/22 |
| 4,516,398 | 5/1985 | Wuchinich | 604/22 |
| 4,559,942 | 2/1985 | Eisenberg | 606/6 |
| 4,583,539 | 4/1986 | Karlin et al. | 606/4 |
| 4,661,093 | 4/1987 | Beck et al. | 604/50 |
| 4,674,498 | 6/1987 | Stasy | 604/22 |
| 4,689,040 | 8/1987 | Thompson | 604/22 |
| 4,729,373 | 3/1988 | Peyman | 604/22 |
| 4,922,902 | 5/1990 | Wuchinich et al. | 604/22 |
| 4,943,290 | 7/1990 | Rexroth et al. | 606/49 |

OTHER PUBLICATIONS

Watkins et al., "Ultrasound Detachment of Calcific Deposits from Diseased Cardiac Valve Specimens", 1960.

W. Young et al., "Acute Physiological Effects of Ultrasonic Vibrations on Nervous Tissues", *Neurosurgery*, vol. 8, No. 6, 1981, pp. 689–694.

Acta Soc. Ophthalmol. Jap., 74(8), pp. 733–738 (Aug. 1970).

Acta Soc. Ophthalmol. Jap., 74(7), pp. 557–661 (Jul. 1970).

Acta Soc. Ophthalmol. Jap., 74(6), pp. 497–503 (Jun. 1970).

Isakovich et al., Sov. Phys.-acoust., 13(3), Apr.–Jun. 1968, pp. 491–494.

Karlin, Ret. Detach. Surg., 73, Nov.–Dec. 1969, pp. 1061–1076.

Kelman, Am. Jour. Ophthal., 64(1), Jul. 1967, pp. 23–35.

Acta. Soc. Ophthalmol. Jap., 74(10), pp. 1313–1327 (Oct. 1970).

Acta. Soc. Ophthalmol. Jap., 73(8), pp. 1165–1183 (Aug. 1969).

Keio. J. Med., 19, pp. 115–133 (Jun. 1970).

Bies, Jour. Acoust. Soc. Am., 34(10), Oct. 1962, pp. 1567–1569.

Karlin, Am. Jour. Ophthal., 68(1), Jul. 1969, pp. 84–91.

Eisner et al., Ultrasonics., Apr.–Jun. 1965, pp. 88–98.

Acta. Soc. Ophthamol. Jap., 74(11), pp. 1484–1488 (Nov. 1970).

Acta. Soc. Ophthamol. Jap., 74(8), pp. 725–732 (Aug. 1970).

Acta. Soc. Ophthamol. Jap., 74(4), pp. 395–401 (Apr. 1970).

Endo-Urology Bulletin, (Richard Wolf), 1984.

Rely on Progress Bulletin, (Richard Wolf), 1984.

Ultrasonic Surgery, Eighth Int'l Cong. Acous., London, 1974.

Personal Interview with Dr. C. D. Kelman (1970).

Vestnik Ophthmologia, 82(5), pp. 20–25 (1969).

Kelman, Am. J. Ophthal., 69(2), (1970), pp. 277–283.

Vestnik Ophalmologia, (82), (5), pp. 26–28 (1969).

Kelman et al., Am. J. Ophthal., 71(6), (1971), pp. 1289–1291.

Frederick, Ultrasonic Engrg., pp. 66–130, 182–183, 308–363, J. Wiley, (1966).

Emery et al., "Phacoemulsification Aspiration of Cataracts", The C.V. Mosby Co., 1979, pp. xi and 5–7.

*Biomedical Ultrasonics*, P. N. T. Wells, London, 1977, pp. 57–58.

E. S. Flamm et al., "Preliminary Experience with Ultrasonic Aspiration in Neurosurgery"; *Neurosurgery*, vol. 2, No. 3, 1978, pp. 240–245.

J. C. Addonizio et al., "Cavitron Ultrasonic Surgical Aspirator", *Urology*, vol. 23, No. 5, May 1984, pp. 417–420.

R. T. Chopp et al., "Use of Ultrasonic Surgical Aspirator in Renal Surgery", Urology, vol. 22, No. 2, Aug. 1983, pp. 157–159.

Bulletin, "Olympus Resectoscope".

Cook et al., "Therapeutic Medical Devices", Prentice-Hall, N.J., 1982, pp. 343–376.

HIGH VELOCITY ULTRASONIC
EXTENSIONAL RESONATOR

STRESS DISTRIBUTIONS FOR VARIOUS
CROSS SECTION AREA VARIATIONS

VELOCITY DISTRIBUTIONS FOR
THE STRESS DISTRIBUTIONS OF FIG. 2

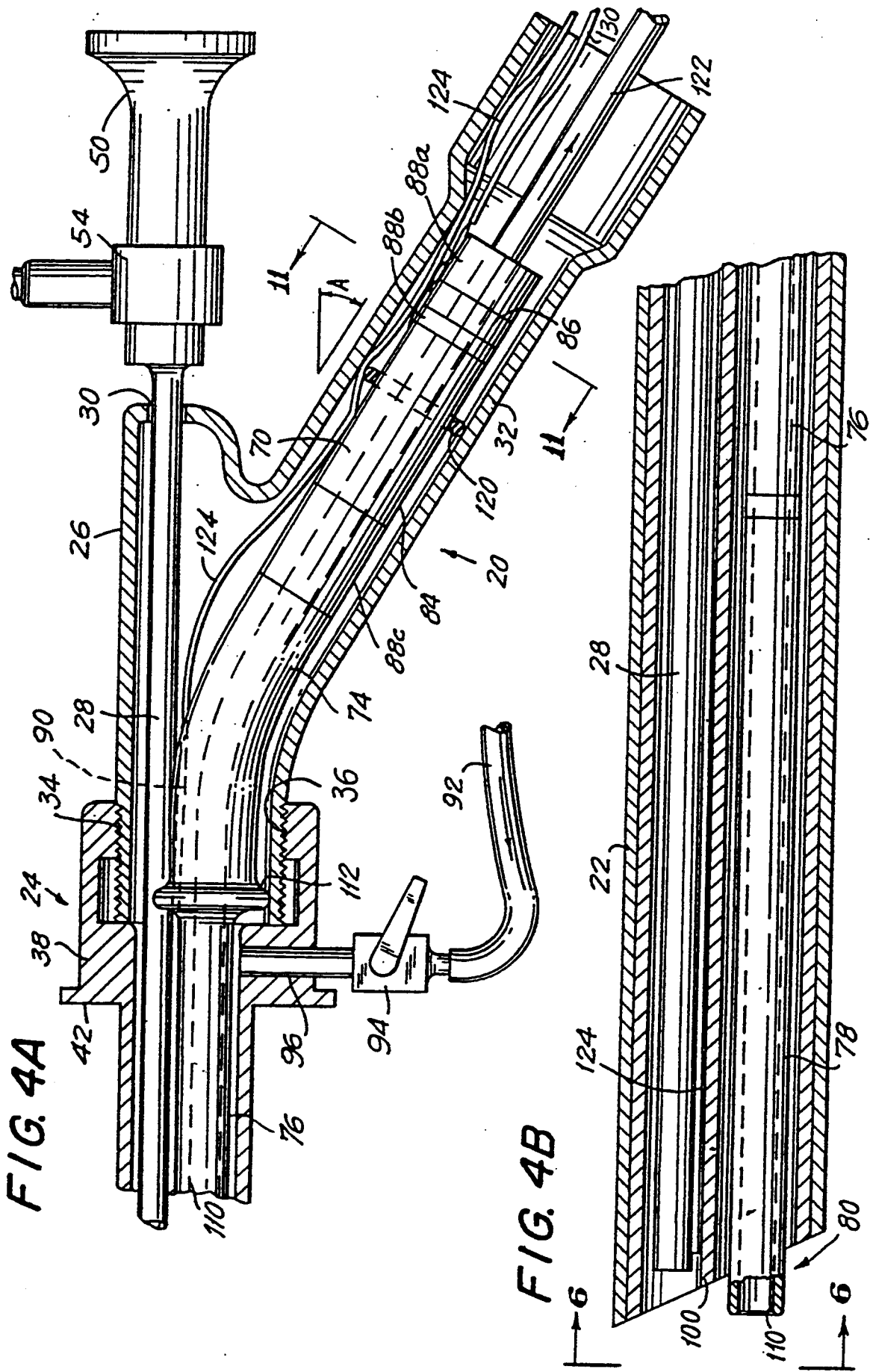

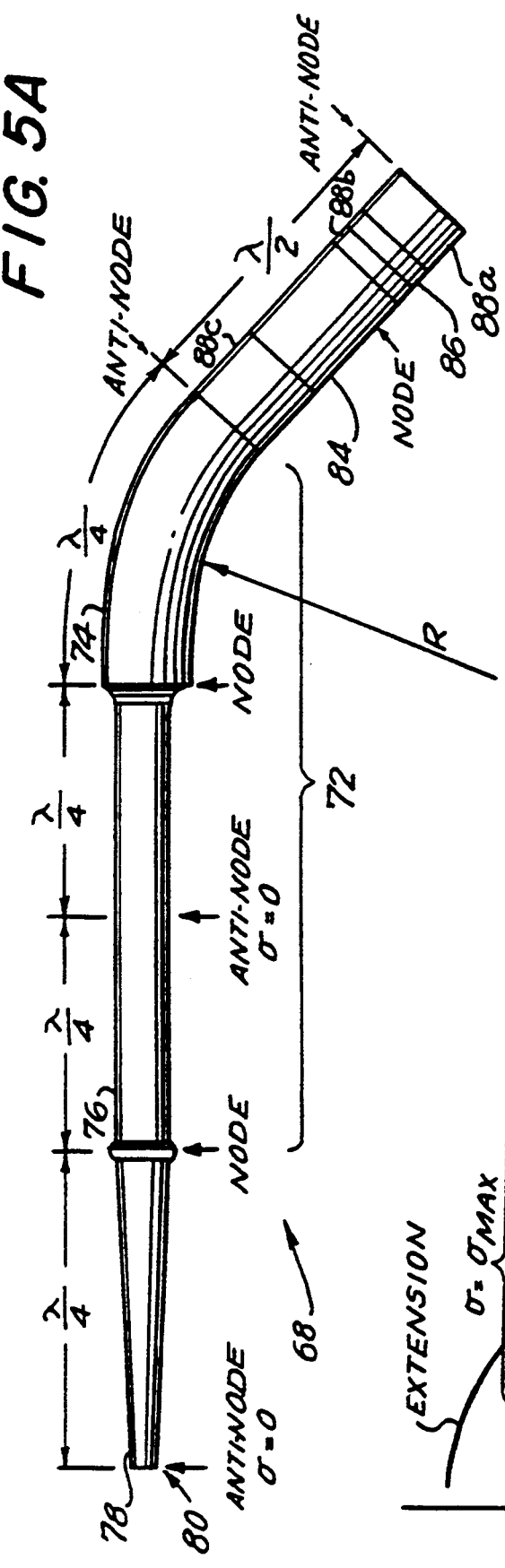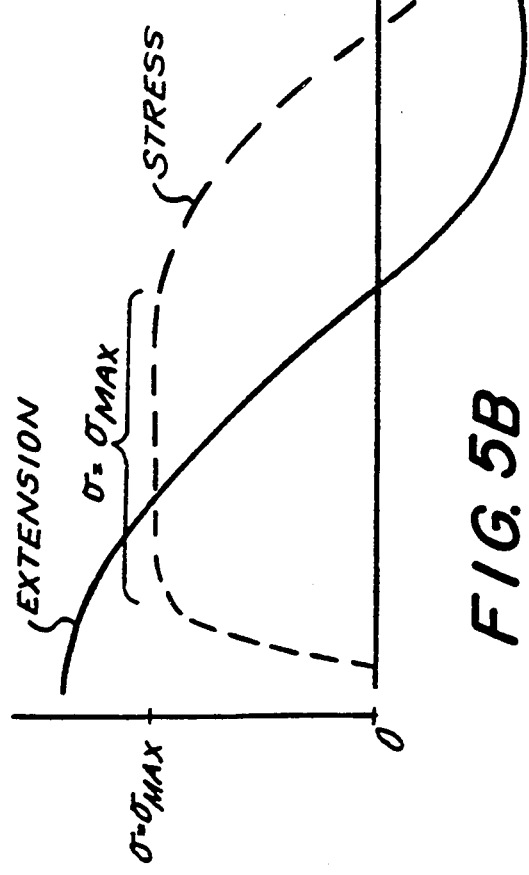

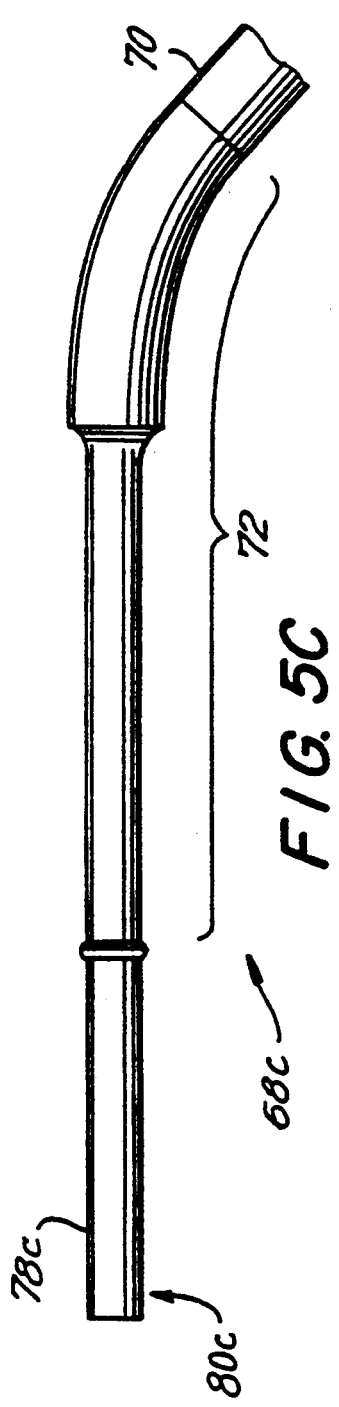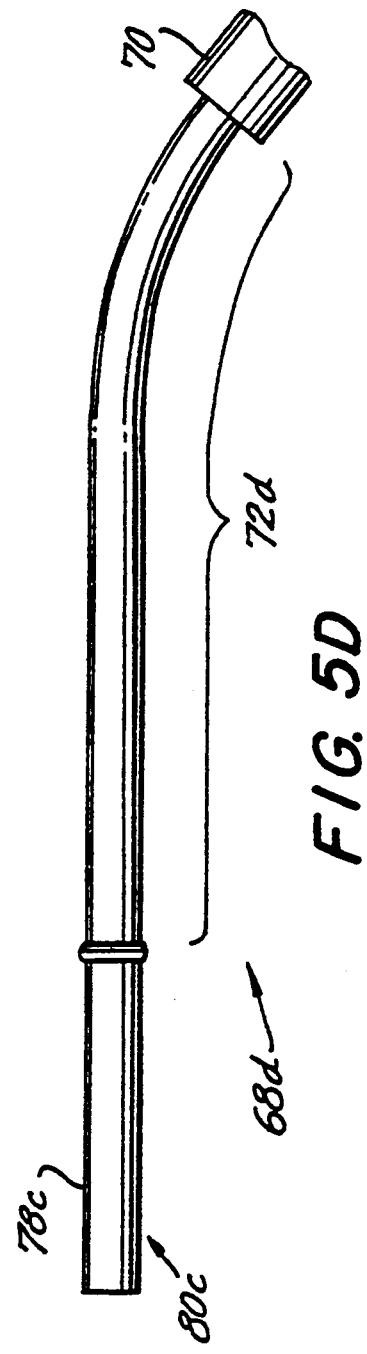

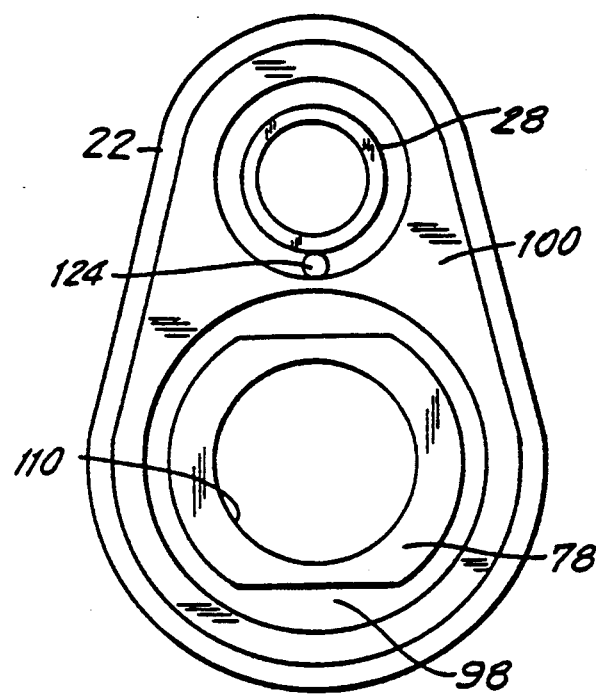
FIG. 6
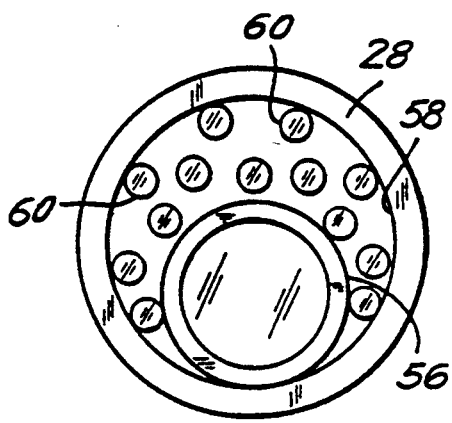
FIG. 7
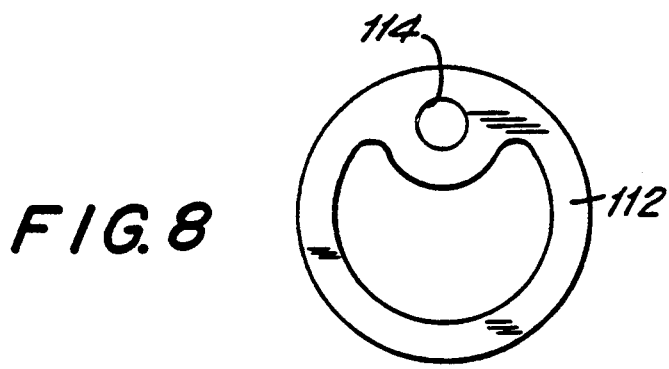
FIG. 8
FIG. 9
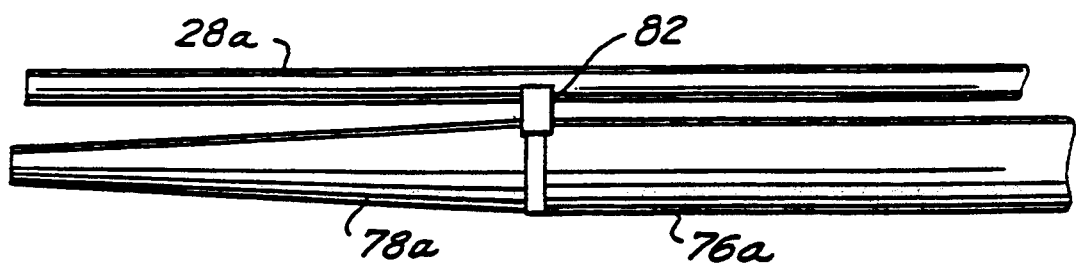

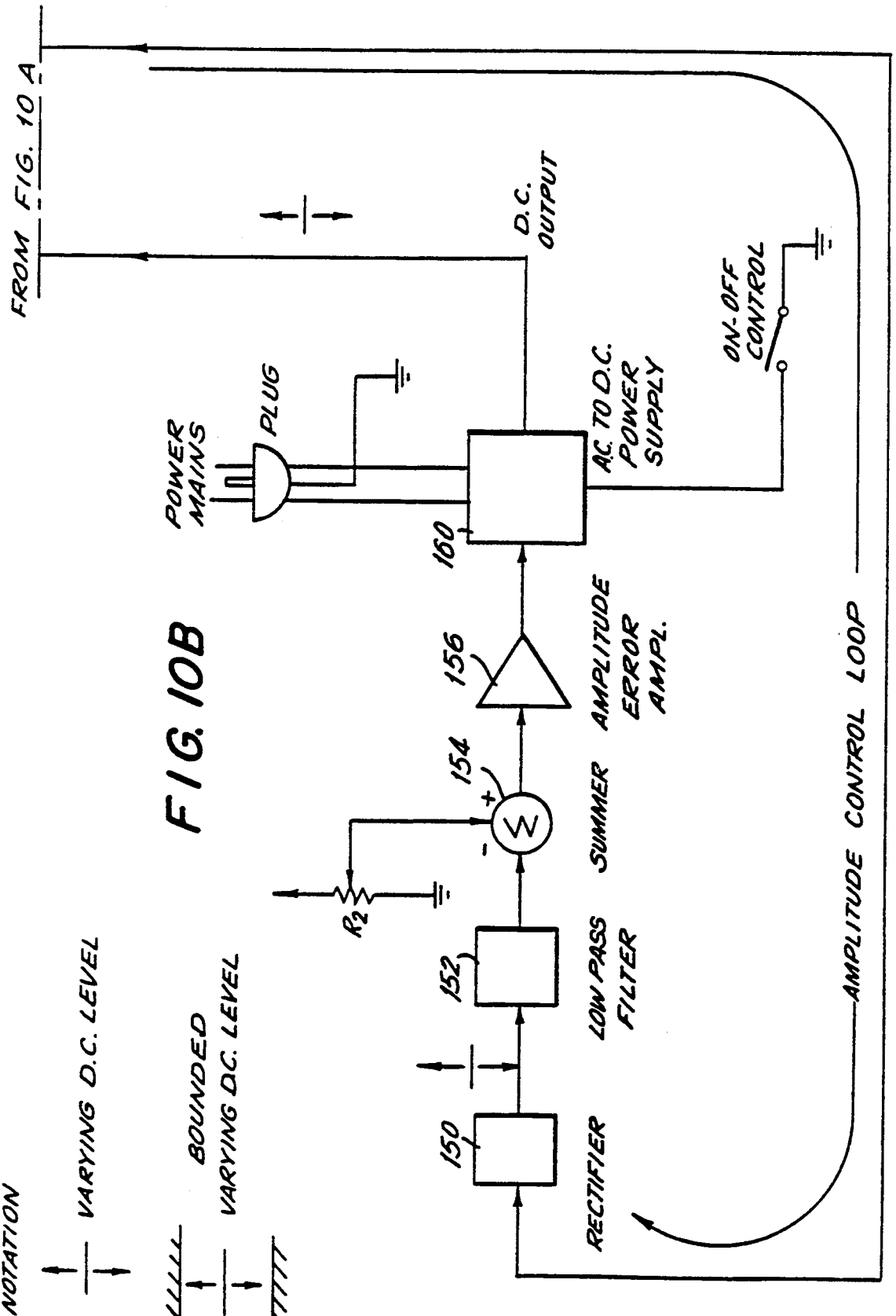

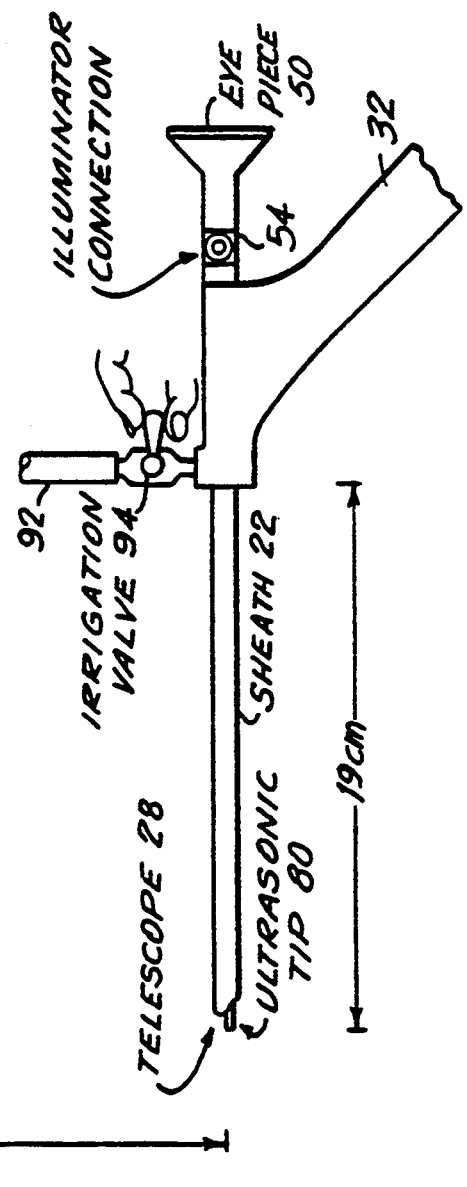
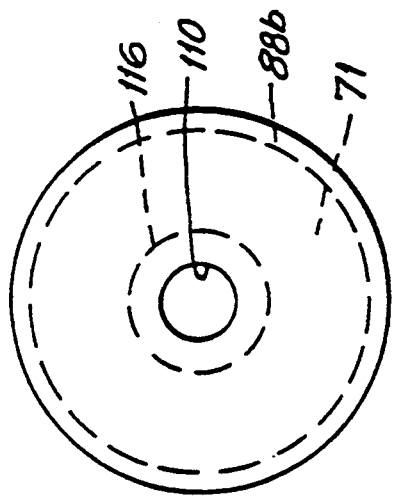

ENDOSCOPIC ELECTROSURGICAL APPARATUS

This is a continuation of application Ser. No. 07/329,747, filed Mar. 28, 1989, now abandoned which is a continuation-in-part of application Ser. No. 07/133,711 filed Dec. 16, 1987, now U.S. Pat. No. 4,922,902, which is a division of application Ser. No. 07/020,266, filed Feb. 27, 1987 now U.S. Pat. No. 4,750,488 and a continuation of application Ser. No. 06/865,240 filed May 19, 1986, now U.S. Pat. No. 4,750,902, which is a continuation-in-part of application Ser. No. 06/770,342, filed Aug. 23, 1985, now abandoned.

TECHNICAL FIELD

The present invention relates to an electro-surgery generator for producing electrical currents for use in surgical applications alone or in combination with an ultrasonic generator, preferably in an endoscopic aspiration device.

BACKGROUND OF THE INVENTION

The use of radio frequency current to cut and cauterize human tissue in surgical procedures was developed by W. T. Bovie and Harvey, Surg. Gyn. and Obs., 47:751–84 (1928). This technique is well known and commonly employed today in many different types of operations.

In endoscopic surgical procedures, an instrument is inserted through a narrow opening made in the body, or through an available natural orifice, such as the throat, rectum or urethra. This instrument contains an integrally illuminated telescope which is used to provide the surgeon with a view of the tissue under consideration. In addition to the telescope, endoscopic instruments usually have working channels to admit one of several different implements: grasping forceps, punches, and electric cutting loops. Of particular interest to this invention is the resectoscope commonly used in urology to remove the prostate and bladder tumors. This instrument is also used in gynecology to remove fibroids of the ureterus as well as to perform percutaneous hysterectomies.

The resectocope is enveloped by a sheath, which is first introduced into the body of the patient. The working implements are then passed through the sheath whose sole function is to act as a conduit of safe passage to the targeted tissue. The working implements are usually joined together into one appliance consisting of: (1) a channel for the telescope, (2) a channel for the electric wire loop and (3) a channel to permit the flow of fluid out of the patient. The space within the sheath not occupied by the appliance is used to provide a passageway for the flow of irrigating fluid into the patient at the surgical site.

Although provision has been made to permit egress of fluid, and thereby to regulate the pressure exerted by the irrigating fluid upon the patient's tissues, the outflow channel can not accommodate the passage of dissected tissue. In procedures in which the resectoscope is used, cut tissue is flushed from the site by the irrigation flow to adjacent open voids, such as the bladder, and later removed using a suction/irrigator, or by simply washing the dissected fragments out of the body using copious irrigation, through the original opening used or made to reach the tissue.

If tissue could be aspirated as it is dissected, several beneficial results would be obtained:
1. Enhanced visibility of the dissection site;
2. A shortened operative time; and
3. The ability to biopsy selected tissue sites.

SUMMARY OF THE INVENTION

Three embodiments of the aspirator of the present invention are contemplated: (1) the use of an ultrasonic vibrator and a radio frequency generator to respectively cut and cauterize tissue simultaneously, (2) the use of an ultrasonic vibrator to cut tissue coupled with the independent use of a radio frequency generator to cut tissue, (3) the exclusive use of a radio frequency generator to cut and cauterize tissue, and (4) the use of a laser to fulgerate tissue. The aspiration system is combined with these embodiments for reasons already discussed.

Thus, the present inventor has shown that a surgical apparatus can be made so as to permit the use of either ultrasonic vibration, electro-surgical current, a laser beam or the simultaneous application of each function. The availability of independent selection of the cutting modality has several important advantages:
1. Electrical cutting can be used to dissect tissue found resistant to ultrasonic attack as, for example, connective tissue of low water content interlacing a tumor or benign growth whose entire removal is sought;
2. Ultrasonic cutting can be employed on tissue near sensitive structures, such as the bladder neck and prostatic capsule, whose removal is never intended, that are resistant to the ultrasonic technique but easily dissected electro-surgically;
3. The simultaneous application of ultrasonic vibration and coagulating current to dissect and seal bleeding tissue; and
4. The use of a laser allows the tissue to be fulgerated: i.e., unwanted cells are destroyed while bleeding of adjacent tissue is stopped.

BRIEF DESCRIPTION OF THE DRAWINGS

Other objects, features, and advantages of the invention will be seen in the following detailed description of preferred embodiments, with reference to the accompanying drawings, wherein:

FIG. 4A and 4B together form a view, partly broken away, of an endoscopic ultrasonic aspirator (EUA) according to an embodiment of the invention;

FIG. 5A is an elevational view of a resonator assembly including a transducer and first and second velocity transformers for use in the EUA of FIGS. 4A and 4B;

FIG. 5B is a graph showing extension and stress distributions in the components of FIG. 5A;

FIG. 5C shows an alternate resonator assembly;

FIG. 5D shows another alternate resonator assembly;

FIG. 6 is an end view of the EUA taken along line 6—6 in FIG. 4B;

FIG. 7 is a detail of FIG. 6 showing an end view of telescope 28 of the EUA;

FIG. 8 is a plan view of a sealing ring 112 employed in the EUA;

FIG. 9 is an elevational view of part of an alternate embodiment of the invention;

FIGS. 10A and 10B together form a block diagram of an ultrasonic power supply for use with the EUA;

FIG. 11 is a cross-sectional view of the EUA taken along line 11—11 of FIG. 4A;

FIG. 12A shows schematically an irrigation system for use with the EUA;

DETAILED DESCRIPTION OF THE PREFERRED EMBODIMENTS

According to one form of the invention, an endoscopic ultrasonic aspirator comprises a hollow handpiece, an elongated sheath having a hollow bore running from the interior of the handpiece to a working end away from the handpiece, a vibration source powered by alternating current, an elongated tool coupled to the vibration source and passing through the hollow bore of the sheath to a work site for transmitting such vibrations, viewing means extending from the handpiece to the work site, means for supplying fluid to a fluid space between the tool means and the hollow bore of the sheath, and fluid detection means for detecting the presence of fluid in the fluid space and terminating the supply of alternating current to stop the vibrations when such fluid is not present.

In another form of the invention, an apparatus for removal of unwanted biological material comprises a handpiece; an elongated sheath extending from the handpiece and having a hollow bore; a vibration source in the handpiece; first and second transformers in the hollow bore for amplifying vibrations from the source to a sufficient velocity to disintegrate unwanted tissue, the vibration means and the two transformers being elongated and having a continuous hollow bore extending along a common longitudinal axis to form (1) a first fluid passage in a space defined between the transformers and the sheath, and (2) a second fluid passage along the common longitudinal axis; means for introducing fluid into one of the fluid passages to irrigate an operating site adjacent a working tip of the second transformer; and means for applying suction to the other of the fluid passages to remove such fluid and such disintegrated unwanted tissue from the operating site. According to a further aspect, the means for applying suction includes a biopsy valve coupled to the fluid passage to which suction is applied for selectively diverting fluid and tissue therefrom, and trap means for receiving and filtering the desired fluid and tissue that has been selectively diverted.

Figure 1:
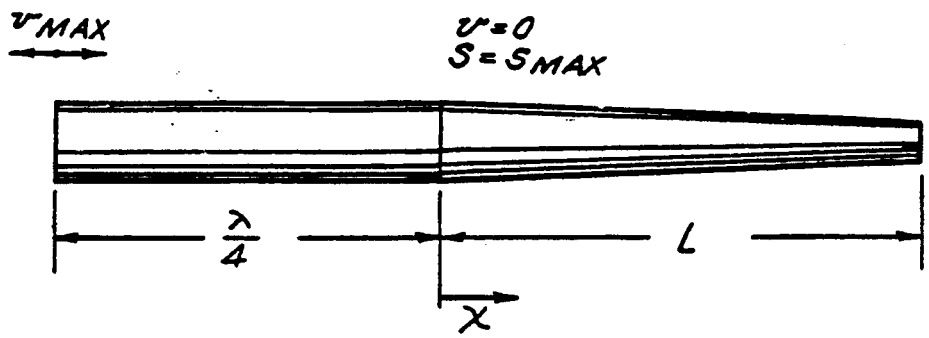
FIG. 1 shows a hypothetical extensional resonator for use in illustrating the background of the invention.
Figure 2:
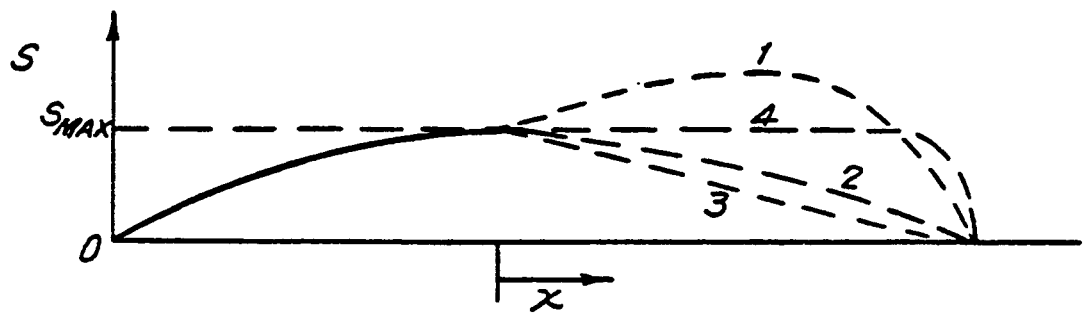
FIG. 2 shows a family of curves illustrating possible stress distributions in the resonator of FIG. 1.
Figure 3:
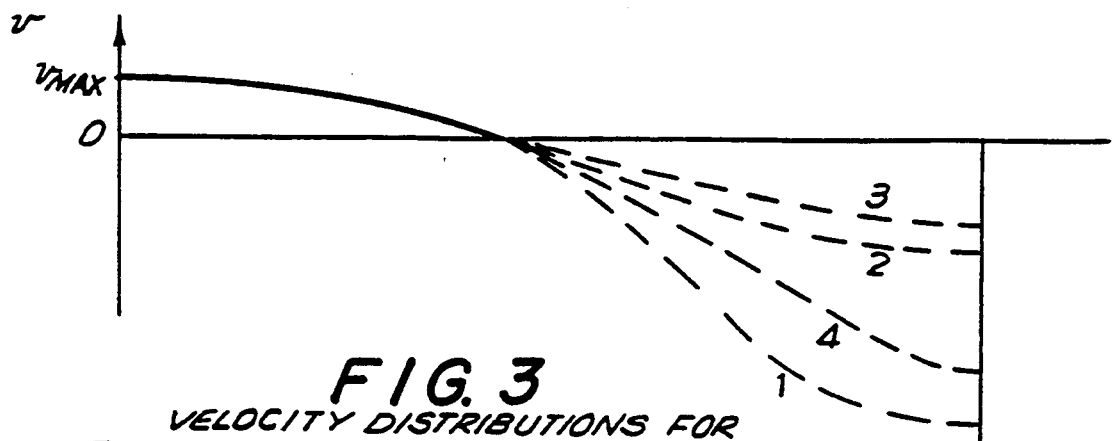
FIG. 3 shows a family of curves illustrating velocity distributions corresponding to the stress distribution curves of FIG. 1.

FIG. 1 shows a hypothetical velocity transformer consisting of a uniform section one-quarter wavelength long, followed by an integral second section of length L. FIG. 2 illustrates various possible stress distributions in this bar for different hypothetical cross-sectional variations of the second section. The velocity at any point to the right of the uniform section can be written as $$v(x) = [-2\pi f/E] \int_o^x s(x)dx \qquad (3)$$

where $s(x=0)=s_{max}$, $s(=L)=0$, f is the frequency of vibration (cycles per unit of time), and E is the elastic constant or Young's Modulus (force per unit area). Thus, the velocity distribution along the section can be computed directly from these stress distributions. The velocity at any point is proportional to the area under the stress curves to that point. FIG. 3 illustrates these corresponding velocity distributions. Curve 1, although it produces the largest end velocity, exceeds $S_{max}$ and therefore is not a practical choice. Curves 2 and 3 produce safe stress distributions, but do not result in the maximum attainable end velocity. The areas under these curves in FIG. 2 are less than the areas under curves 1 and 4.

Curve 4 alone increases the velocity most rapidly while maintaining a safe operating stress. Curve 4 represents a constant stress level section, except at the terminus, which is free and therefore is not subject to any force. Constant-stress amplification can also be achieved in a uniform structure such as a cylindrical tube by varying the elastic constant E, or both the electric constant E and the density p, over the length of the structure, without varying the cross-sectional area.

FIGS. 4A and 4B shows an endoscopic ultrasonic aspirator according to a preferred embodiment of the invention. A handpiece 20 is located at what will be referred to as the rear end of the device. A sheath 22 extends from the handpiece 20 toward what will be referred to as the working end of the device. A stop assembly 24, integral with the sheath 22, couples the handpiece to the sheath. The handpiece is preferably plastic and the stop assembly and sheath are preferably metal. The EUA also includes a straight telescope 28 which runs horizontally from the rear end to the working end of the EUA. A horizontal upper lobe 26 of the handpiece 20 contains an aperture 30 through which the telescope passes to the exterior of the handpiece. The handpiece also has a lower lobe 32 which forms an angle A with the upper lobe 26. Angle A may advantageously be about 20 to 45 degrees, its purpose being to allow various components to be located within the handpiece without interfering with the straight horizontal line of sight occupied by the telescope.

The sheath 22 is assembled to the handpiece 20 by means of a stop assembly 24, which is integral with the sheath 22 at its rear end. The stop assembly 24 is generally cylindrical and has a circular aperture in its rear side with inward-facing threads 34. The handpiece is circular at its forward end and has outward-facing threads 36 which are adapted for screw-mounting in the threads 34 in stop 24. The stop 24 has a forward portion 38 with annular faces 40 and 42 which face rearward and forward, respectively. The handpiece is screwed into the rear aperture 30 of the stop assembly until it comes into contact with the rear face 40. The front face 42 of stop 24 limits the distance to which the working end of the sheath 22 of the EUA can be inserted into a surgical orifice.

Figure 15:
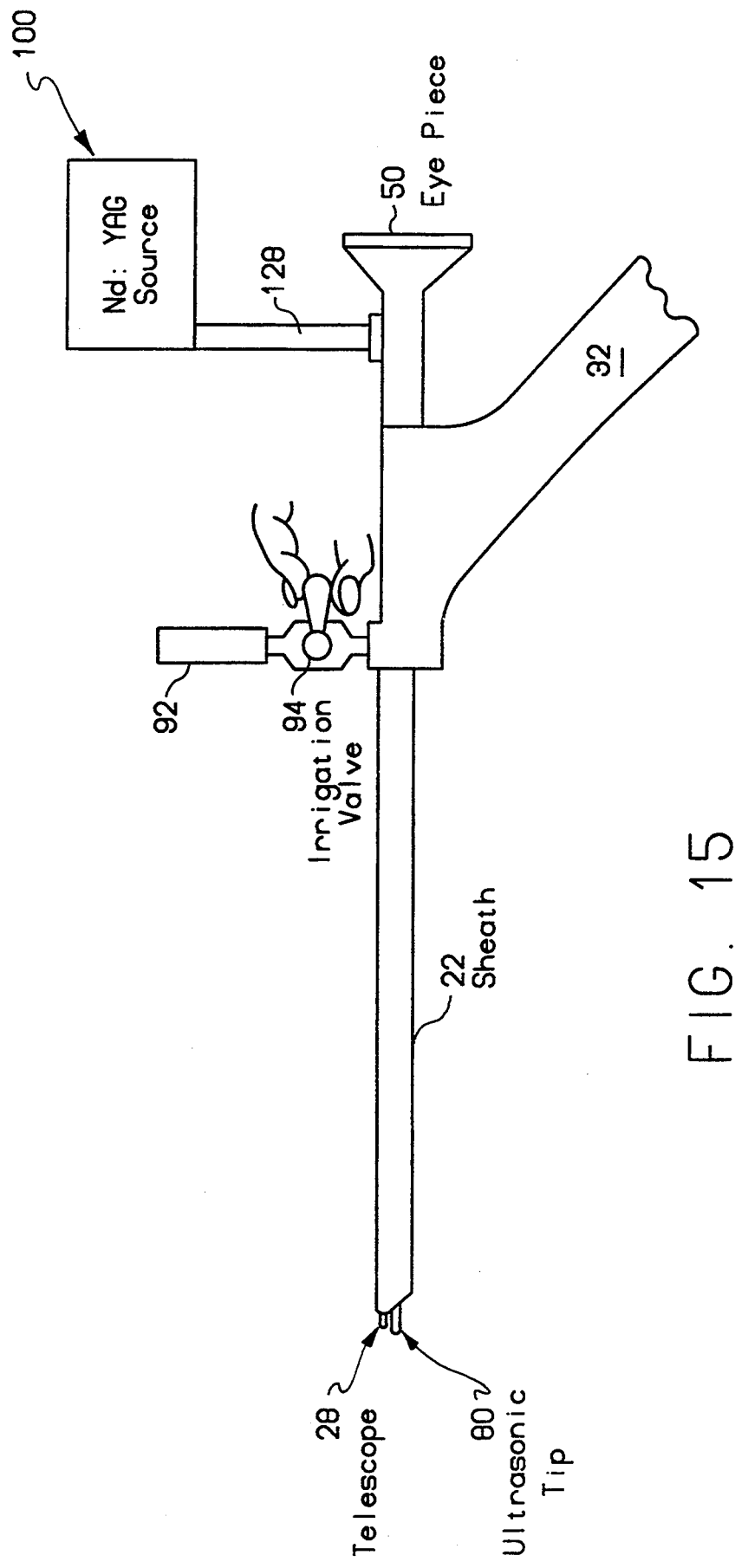
FIG. 15 illustrates the inclusion of a laser in the EUA for fulgurating tissue.

The telescope 28 has at its rear end an eyepiece 50 and a cable 52 for supplying electrical energy to an electro-optical light source 54. From the eyepiece the telescope extends forward in a straight line of sight to the working end of the EUA. The design of the telescope is shown in more detail in FIG. 7. The telescope includes a cylindrical lens system 56 which is located adjacent the lower portion of the cylindrical inner surface 58 of the cylindrical telescope 28. In the crescent-shaped space between the inner surface 58 and the lens system are disposed optical fibers 60 which carry light from the light source 54 to the working end of the telescope. Other illuminating sources may be provided, including laser energy when tissue is to be fulgurated, as shown in FIG. 15. In this embodiment, the outside diameter of the telescope 28 is approximately 3–4 mm, and the outside diameter of the lens system 56 is about 1.7–2.7 mm, depending on the size of the overall telescope 28.

Disposed within the handpiece and sheath is a resonator assembly generally designated 68. The resonator assembly 68, which is seen more clearly in FIG. 5, includes a piezoelectric transducer 70; a first velocity transformer 72 having a relatively thick curved input section 74 coupled to the transducer for receiving vibrational energy therefrom, and an integral narrower output section 76 extending forwardly of the input section 74; and, integrally connected to the forward end of the output section 76, a second velocity transformer 78, which extends from the output section 76 to the working end of the EUA and protrudes slightly beyond the sheath 22. The transducer's length is substantially one-half of the wavelength of the vibrations employed in the device. Thus, the transducer has vibrational antinodes (loops) antis ends and a vibrational node halfway between its ends. The length of the curved input section 74 of the first transformer 72 is one-quarter wavelength; thus, its point of connection with the transducer 70 is an antinode, and the point of connection to the output section 76 is a vibrational node. The length of the output section 76 is one-half wavelength. Thus, an antinode is at the center of this section, and a node exists where it is connected to the second velocity transformer 78.

The second transformer 78 is of the Gaussian type described above. As seen in the schematic graph of FIG. 5, there is little longitudinal extension and little stress in the input section 74, because it is relatively missive and a substantial amount of its vibration is flexural. Stress is high at both ends of the output section of the first transformer, but is zero at its center point, which is a vibrational antinode or loop with greatest longitudinal extension. The stress in the output section 76 is at the maximum permissible level for the material and design employed, in other words $S_{max}$, as defined above. The Gaussian resonator 78 exhibits constant stress at this same level $S_{max}$ throughout most of its length, almost to the tip 80 at its working end. The stress near the tip 80 is substantially zero, since there is ordinarily little or no load on the tip.

As seen in FIG. 6, the second transformer 78 and also the output section 76 are not round, Rather, flats are formed in the top and bottom of these members to provide ample water passages without substantially changing their vibratory characteristics. The central bore 110, however, is substantially circular, with an inside diameter of about 4.33 mm (13 French). The working end 80 need not lie in a vertical plane as shown, but may be angled or otherwise shaped if desired in a particular application. The combined length of the output section 76 and the second transformer 78 is advantageously about 19 cm. If desired, it could be lengthened by any integral multiple of one-half wavelength, which at about 20 kHz is about 13 cm.

A piezoelectric transducer such as is used herein typically has a maximum vibration amplitude of about 23 microns. At the frequencies of intersect, tip vibration at the necessary velocity entails an amplitude of about 350 microns. The resonator assembly 68 provides this 15-fold increase in vibration amplitude.

A groove 90 is formed in the top of the transformer input section 74 and is sized to accommodate the telescope. The groove 90 permits the telescope to relocated closely parallel to the transformer sections 76 and 78 within the forward end of the sheath, without interfering with the input section 74, to achieve a compact and narrow sheath.

The letter R in FIG. 5A refers to the radius of curvature of the curved input section 74. This radius must be small enough so that the handpiece is curved far enough below the line of sight of the telescope, desirable at least about 20 degrees, to achieve a compact and easily handled unit. A radius R of about 5 cm advantageously gives an angle of about 40°. At an operating frequency of 20 kHz, 5 cm is about 0.2 times the wavelength. Preferably, the radius R should be no smaller than about 0.1 times the operating wavelength to avoid excessive energy losses. The radius should also belies than about 0.5 times the wavelengths in order to give usable angle of offset of about 20° over the length of the input section 74, which is about 6 cm. The curvature of the input section is not necessarily circular; thus, the radius R as defined herein is an approximation.

FIGS. 5C and 5D shows alternate resonator assemblies 68c and 68d. In FIG. 5C, a first transformer 72 is coupled to a transducer 70. As in the previous embodiment, the first transformer is a half-wave stepped transformer. Coupled to the working end of the first transformer is a second transformer. Coupled to the working end of the first transformer is a second transformer 78c, which has constant cross-sectional area. Velocity amplification is obtained by increasing the elastic constant of the material in the second transformer from its point of connection to the first transformer, to its tip 80c. Optionally, the density of the material of the first transformer may be decreased as a function of distance from the first transformer to the tip.

In the embodiment of FIG. 5D, the same second transformer 78c as just described is employed. However, in this embodiment the first transformer 72d, which is curved as in the previous embodiments, is not a stepped transformer. Rather, velocity amplification in the first transformer is obtained by increasing the elasticity of the material of the first transformer and optionally decreasing the density of the material, as a function of distance from the transducer. As seen in FIG. 5D, the transducer 70 and the first transformer 72d are not necessarily required throve the same cross-sectional area at their coupling for sufficient energy transfer to be obtained.

Because of the curvature of the section 74, the transformer sections 74, 76, 78 may undergo a certain small amount of transverse, flexural vibrations. However, any transverse components of vibration in the sections 76 and 78 are damped by the presence of irrigation fluid in the surrounding fluid space 98 within the sheath.

Irrigation fluid is supplied through a hose 92, and is controlled by a valve 94. The irrigation fluid flows through a radial bore 96 in the outer portion of the front section 38 of the stop assembly 24. It than passes into the spaces 98 that surround the resonators 76 and 78 within the sheath. As indicated generally in FIG. 6, the sheath has a generally ovoid cross-section. Its circumference should preferably be approximately 25 mm, about the same as the circumference of a circular instrument 8 mm in diameter, such dimension being known in the field as 24 French. If necessary, a circumference of about 29 mm, corresponding to 28 French, may be usable. With 28 French or larger instruments, there is a risk of injury to a narrow orifice schwas the urethra. The telescope 28 is disposed in the narrower part of the ovoid sheath 22. It is enclosed by epoxy material or the like running along the inside of the sheath to form a partition 100, which forms a watertight compartment for the telescope.

Irrigation fluid flows toward the working end of the EUA through the space 98 from the vicinity of the stop 24, damping any transverse vibrations of the transformer sections 76 and 78, as well as irrigating an operating site adjacent the tip 80. Auxiliary fluid passages may also be provided. Fluid is prevented from flowing into the handpiece by a sealing ring 112 shown in FIG. 8. The ring is generally O-shaped, but has a smaller aperture formed in its upper portion to accommodate the telescope. The sealing ring 112 seals the annular space surrounding the input transformer section 74 within the handpiece, and provides the hole 114 for water-tight passage of the telescope. Additional sealing and support is provided by an O-ring 120 disposed about the transducer within the inner wall of the lower handpiece lobe 32. The O-ring 120 is located at the vibrational node at the center of the transducer.

The coupling between the transducer and the input section 74 may advantageously include female threads counterbored into the abutting ends of the aspiration passages 110 of the transducer and the input section, and a hollow threaded stud threaded into both of these. Such a connection allows for smooth, fine finish of the adjacent faces of these two resonator elements, for good acoustic coupling between the faces.

Referring again in FIGS. 4A and 4B, aspiration is provided through a continuous concentric bore 110 extending from the tip 80 through the second transformer 78, the first transformer 72, and the transducer 70 to a hose 122, which is connected to a source of suction. Other passages may be provided as well. By these means, fluid and removed tissue flow from the operative site and are aspirated through the EUA away from the operating site for either disposal or histological analysis. The edges of the working end of the second transformer 78 at the tip 80 are rounded, in order to provide tissue removal by cavitation of intercellular water, as discussed previously, without allowing indiscriminate cutting by the tip 80, which could inadvertently injure tissues not intended to be removed.

It is important for any transverse vibration components of the transformer section 76 and 78 to be damped by fluid flowing in the spaces 98, and for vibration terminate if there is no fluid present. For this purpose, a fluid sensor is provided in the form of an insulated wire 124 running rearward along the telescope, and separated from the fluid space 98 by the partition 100. The wire 124 runs through the hole 114 in the sealing ring 112, and through the groove 90 in the input section 74, to the interior of the handpiece. The wire could also be set into a groove either in the partition 100, in the bore that encloses the telescope, or in the bore that encloses the resonators, if desired. It may also be exposed to fluid if appropriate insulation is provided. The wire is fine enough that it does not interfere with the seal provided by the sealing ring 112. The wire 124 then passes around the O-ring 120 to the exterior of the handpiece. As explained further below, means are provided in the high-frequency power supply circuit to sense the capacitance between this wire 124 and the second transformer 78, which is grounded. If the capacitance increases, which indicates the absence of water, then the vibration of the transducer 70 is inhibited to prevent excessive transverse vibrations and possible damage to the resonator components.

FIG. 9 shows elements of an alternate embodiment of the invention. In this embodiment, there is no partition between the telescope 28a and the irrigation-fluid-containing space that encloses the resonators 76a, 78a. To support the telescope, a quantity 82 of biologically inert silicone rubber adhesive or the like is placed between the telescope and the junction of the resonators 76a and 78a. It is important to employ a flexible adhesive to allow some relative motion, even though this junction is a vibrational node, since each point on each resonator is subject to a small degree of radial vibration, which is inherent in a body undergoing extensional vibration. As each incremental section of a resonator is compressed it instantaneously bulges slightly. Thus, each point on each velocity transformer constantly undergoes a slight radial expansion and contraction. These radial vibrations should be isolated from the telescope. However, there cannot be more than about 250–500 microns of separation between the telescope and the resonators because of the severe size limitation on the sheath. This need for proximity, in view of the further need for vibrational isolation, is resolved by connecting the elements with a flexible adhesive.

Figure 10A:
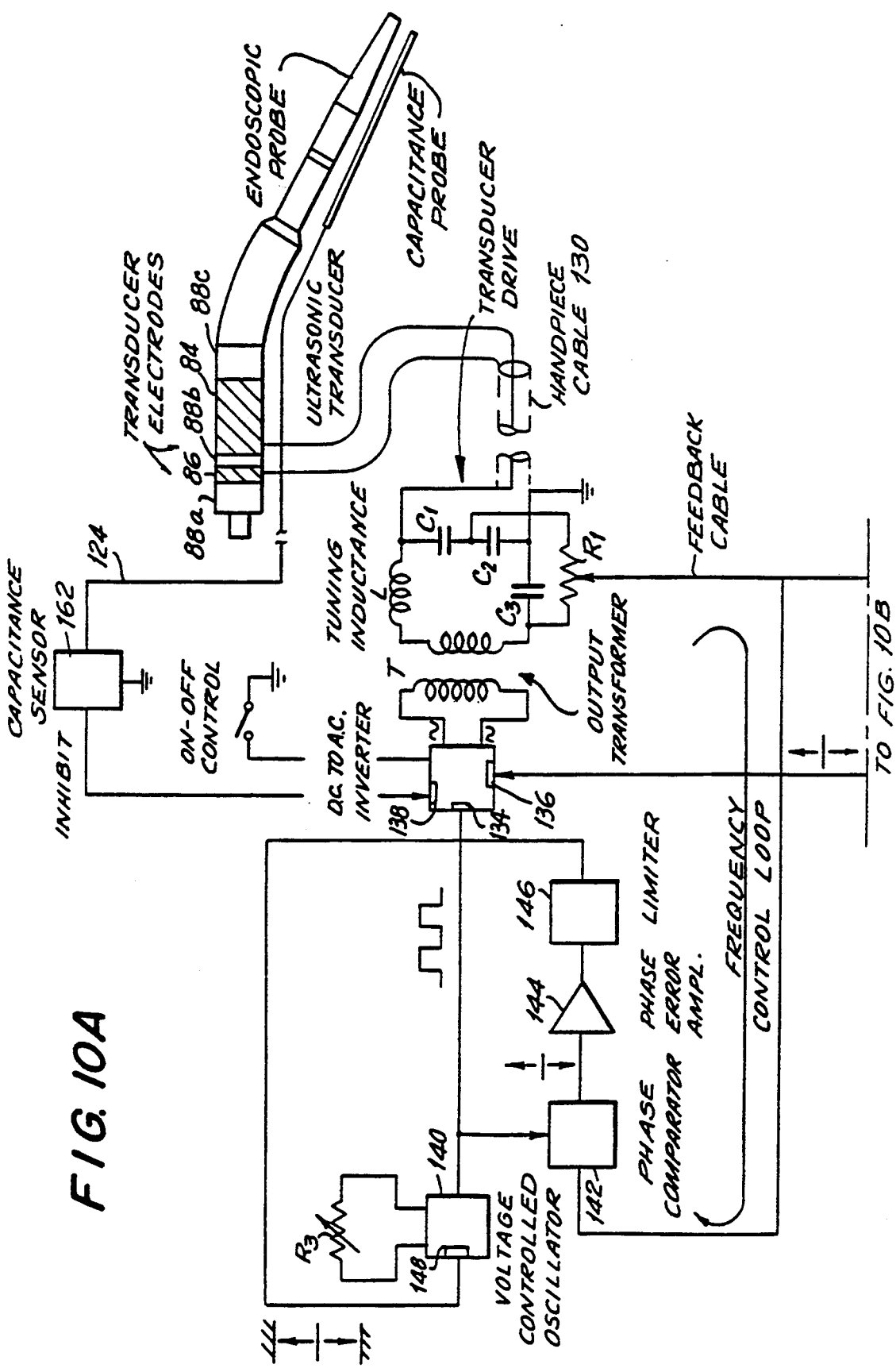

The ultrasonic generator and related circuitry for powering and controlling the ultrasonic transducer 70 are shown in FIGS. 10A and 10B. The transducer 70 includes an elongated toroidal piezoelectric crystal 71 that is driven by a cylindrical high-voltage electrode 84 and an annular ground electrode 86. (see also FIGS. 4A and 11.) The ground electrode 86 is electrically connected to a conductive lining 116. The lining 116 runs the length of the transducer 70, lining the aspiration passage 110, and is electrically coupled to the velocity transformers. The transducer is insulated by cylindrical insulators 88a, 88b, 88c located at the ends of the transducer and between the electrodes 84 and 86.

The piezoelectric transducer and tip are driven by the generator through a two-conductor coaxial cable 130. It is energized by an AC signal whose magnitude and frequency are controlled by a DC-to-AC inverter 132. This inverter creates an input DC voltage to an alternating current signal having a frequency controlled by an AC signal supplied to its frequency control input 134 and a magnitude controlled by a DC voltage level supplied to the inverter at its magnitude control input 136. The frequency provided at the input 134 is the frequency at which the transducer is caused to vibrate. The DC voltage supplied at the input 136 is that required to maintain a selected amplitude of vibration at the frequency of vibration.

The exciting frequency and voltage are derived from a feedback signal obtained by adding two signals that are proportional to the voltage and current input to the transducer. In FIG. 10, $C_1$ and $C_2$ form a capacitive voltage divider which produces a voltage across $C_2$ that is directly proportional to and in phase with the transducer voltage. The voltage across $C_3$ is proportional to the transducer current, but shifted in phase by 90 degrees. The voltage between the wiper of potentiometer $R_1$ and ground, which constitutes the sum of these two potentials, is the feedback signal. When $R_1$ is properly set, the feedback signal is very low at all excitation frequencies except at the resonant frequency of the transducer, since at resonance the transducer voltage and current are 90 degrees out of phase.

At resonance, when the feedback signal is present, its magnitude is proportional to the amplitude of vibration and its phase exactly equals that of the inverter output signal. The inductance L reactively cancels the transducer's static capacitance; that is, the capacitance of the cable 130 and the net capacitance of the voltage divider $C_1$, $C_2$. This capacitance is advantageously neutralized so that the voltage at the wiper of $R_1$ will be proportional to the vibration amplitude and will be very small at frequencies other than resonance.

The feedback signal is fed to two control loops: one for establishing the correct frequency and the other for establishing the desired vibration amplitude. When the aspirator is de-energized there is of course no feedback signal, and some means of starting vibration has to be provided. A predetermined starting frequency is provided by a voltage-controlled oscillator 140. In the absence of any feedback, this oscillator runs at a frequency adjusted by variable resistor $R_3$ in the general range of the expected transducer resonance. Since, in general, this initial exciting frequency is not the resonant frequency, a substantial feedback signal will not be produced. However, acoustic resonators do exhibit some greatly diminished level of vibration at frequencies within about five percent of their actual resonance. Therefore, a small, but detectable, feedback signal is produced.

In the frequency control loop, the feedback signal enters a very sensitive phase comparator 142 which produces a DC voltage proportional to the difference between the phase of the feedback signal and the phase of the output of the voltage-controlled oscillator. The frequency of the feedback signal is the same as that of the oscillator, but the phase is not the same because the frequency is not yet at the resonant frequency of the transducer. The output from the phase comparator is greatly amplified by phase error amplifier 144 and then passed through a limiter 146 which places upper and lower bounds upon the amplifier's output. This amplified signal, subject to the bounds of the limiter, is then supplied to a steering input 148 of the voltage-controller oscillator 140, and modifies its output frequency until the phase difference between the feedback signal and the output signal of the VCO is minimized. The VCO frequency that produces this result is the actual resonant frequency of the transducer.

The result of limiting the range of the steering voltage applied to the oscillator at input 148 is to limit the extent to which the frequency can be shifted. In general, a complex acoustic resonator, such as transducer 70, has more than one extensional resonance, at only one of which the desired performance is obtained. Excitation at other resonant frequencies would result in much lower vibration levels and very poor tissue dissection. Because the vibration levels are much lower at these parasitic resonances and constitute a lower overall energy of vibration, if precautions were not taken, the system would naturally tend to operate at frequencies where it did less work. The limiter 146 prevents the oscillator from being driven to frequencies that lie outside a predetermined band which brackets the intended resonance.

In the amplitude control loop, the feedback signal is fed to a rectifier 150 which produces a DC voltage proportional to the magnitude of the feedback signal. A low-pass filter 152 is provided to eliminate any AC components and extract only the direct current component. This signal is then subtracted by a summer 154 from a preselected DC voltage. The difference between these two voltages is greatly amplified by an amplitude error amplifier 156 and is input to the main power supply 160 to control its DC output voltage. This DC output voltage is the source of power to the inverter 132. It is proportional to the magnitude of the inverter's AC output signal, which, in turn, is proportional to the amplitude of vibration of the transducer 70. This amplitude control loop maintains the amplitude of vibration desired by the operator regardless of the power drawn from the inverter 132 by the transducer 70, thereby providing uniform performance in the presence of compliant as well as resistant tissue. Since the power available from the inverter is to limitless, internal circuitry is provided in this component to safely limit the maximum power consumption by the transducer, and thus preclude unsafe power demands through intentional or unintentional abuse. If the power limit of the inverter is reached, the output vibration amplitude is automatically reduced. The amplitude is reestablished at the control setting once the excessive power requirement has been removed.

Also seen in FIG. 10A is a capacitance sensor 162 which measures the capacitance between the capacitance probe 124 and ground. When this capacitance increases substantially, indicating the absence of water surrounding the velocity transformers 72 and 78, the capacitance sensor 162 sets the input level at an input 138 of the inverter 132 to a level that inhibits the inverter and terminates the AC output to the transducer.

Figure 12B:
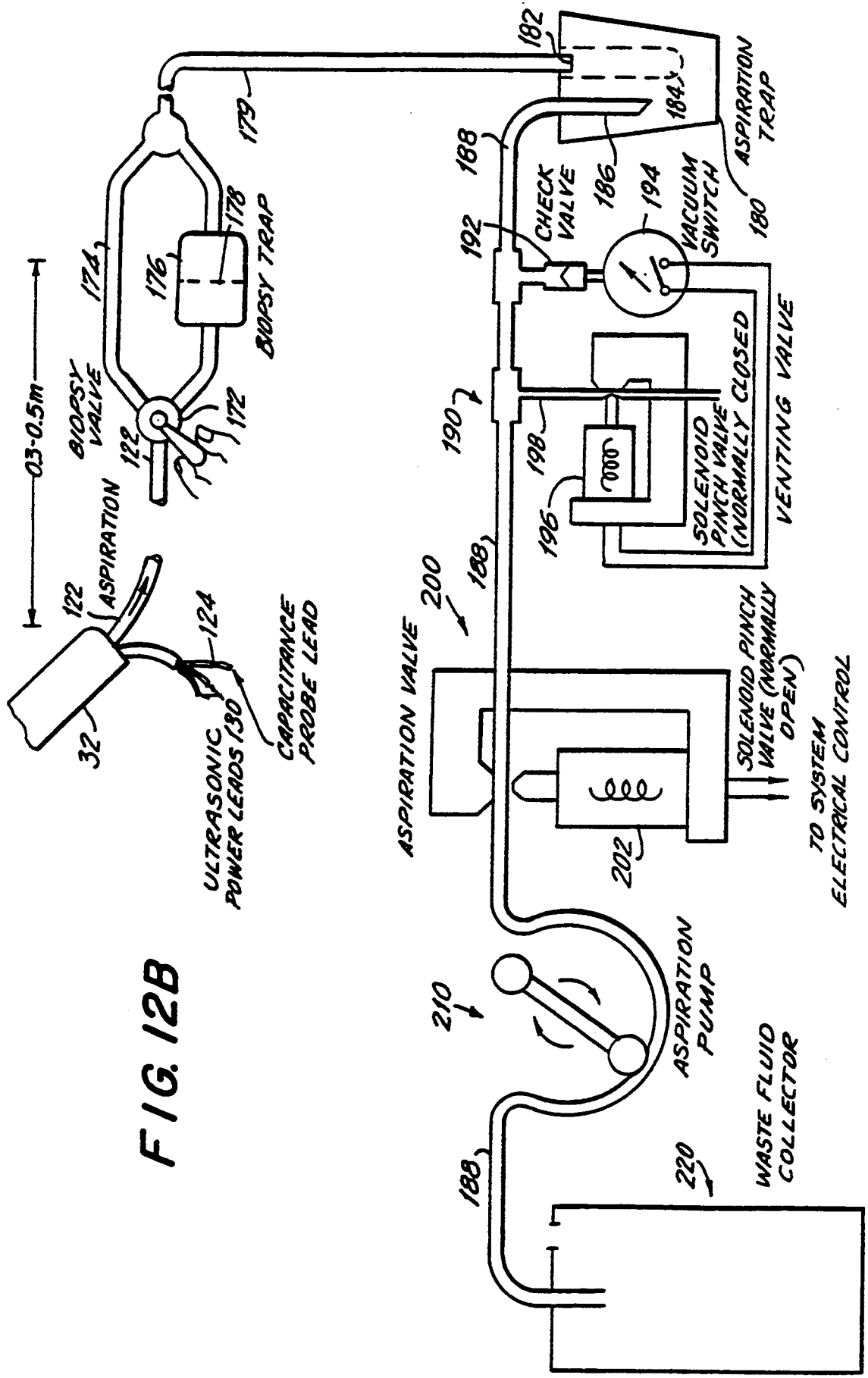
FIG. 12B shows schematically an aspiration system for use with the EUA.

FIG. 12 illustrates an overall endoscopic ultrasonic aspiration system. An irrigation fluid source 170 is located about 1-2 meters above the EUA. This distance provides sufficient hydrostatic pressure to keep the bladder neither distended nor collapsed. Aspirated fluid and tissue pass through the aspiration hose 122 to a two-position biopsy valve 172. Ordinarily, debris will be directed by the valve 172 through a direct hose 174 toward the source of suction. However, when the surgeon sees suspected tissue of which a biopsy would be desirable, the valve 172 can be thrown to direct the debris to a biopsy trap 176. The biopsy trap is a watertight vessel having a transverse screen 178 through which the aspirated debris must pass. The desired tissue can be rapidly collected on the screen and taken away for histological analysis. The biopsy trap should be relatively close to the EUA, for example about 0.3 to 0.5 meter. Because it is close, the hose 122 can clear very rapidly so that the biopsy material can be collected without unnecessary delay after the suspect tissue is spotted. The trap can also be kept sterile so that samples can be collected without contaminating either the sample itself or the surgeon's gloves.

The aspirated debris then passes through a line 179 to the main aspiration trap 180. The trap 810 is a closed vessel having an inlet 182 surrounded by a sock-shaped screen 184, which filters the debris. After filtration, tissue can be removed for medical examination in bulk. The trap has an outlet 186 away from the screen 184.

The screens 178 and 184 are not particularly fine. Their openings may advantageously be about 1 mm square so as to pass blood clots, etc., without clogging. On the other hand, the screen gauge is selected to trap pieces of tissue whose size is about the same as the inside diameter of the working tip 80, which is about the dimension of the tissue that is cored out of the organ being resected.

After filtration, the debris passes through a line 188 to a venting valve 190. The valve 190 has a check valve 192, which opens and passes the pressure on the line 188 to a vacuum switch 194 if the pressure on the line 188 falls to a predetermined low level, which would indicate that the system is clogged. If the vacuum switch 194 opens, a solenoid 196 opens, and this opens a vent line 198, which vents the aspiration pressure to the atmosphere. Overall control of aspiration pressure is provided by a main valve 200 operated by a solenoid 202. Pumping is provided by a peristaltic pump 210. Waste aspiration fluid is received in a collecting vessel 220.

FIG. 15 illustrates a handpiece similar to that of FIG. 12A except that a laser energy generating source 100 is utilized to provide laser energy through optical fiber 128 and telescope 28. This allows the laser energy to be directed to the work site for fulgurating tissue in combination with the vibrating tip 80. If desired, the optical fiber used for transmitting the laser energy can be placed outside of the sheath. This arrangement allows the viewing means and laser energy to be utilized simultaneously.

Figure 13:
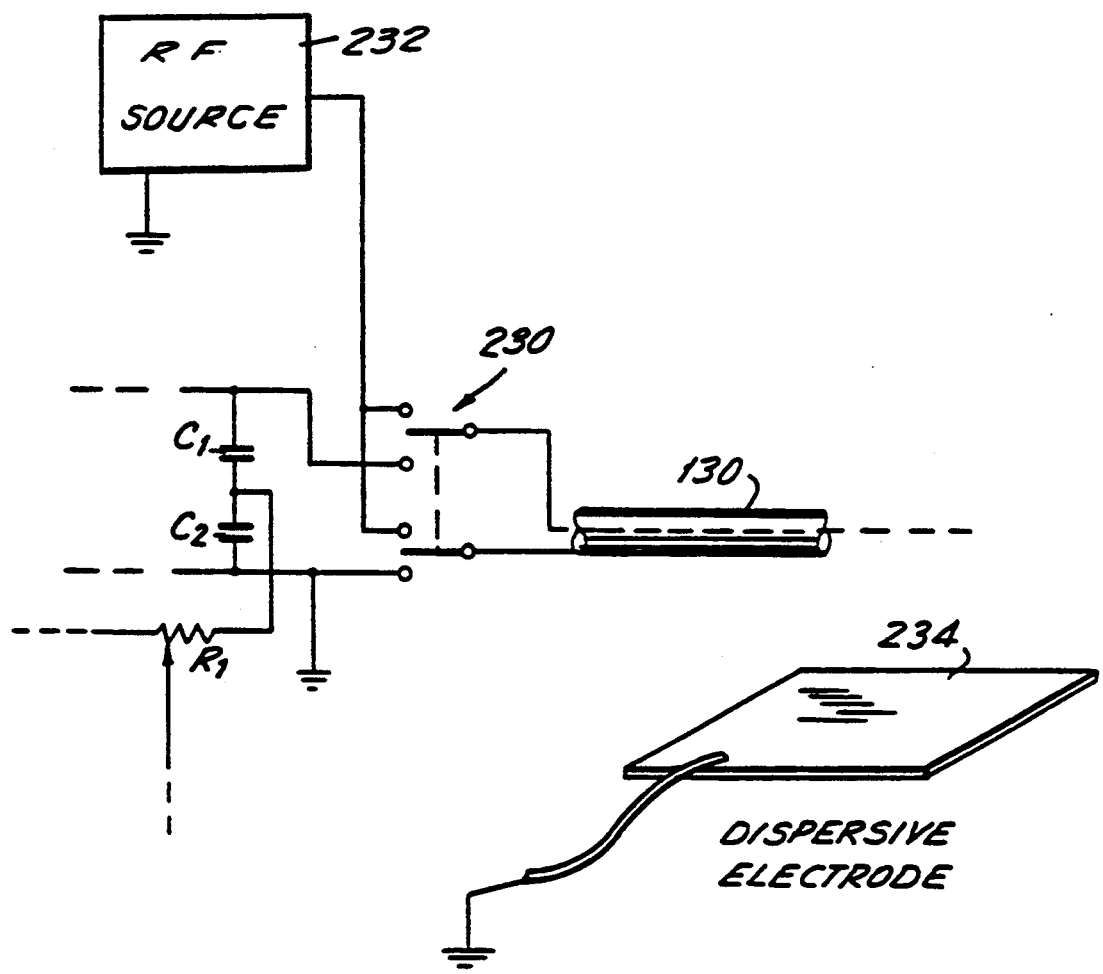
FIG. 13 is a schematic diagram of part of an alternate ultrasonic power supply for use with the endoscopic ultrasonic aspirator.

The embodiments of the present invention may be operated using an endoscopic ultrasonic aspirator ("EUA") similar to that taught in U.S. Pat. No. 4,750,902 and as described above. While this patent discloses a method of incorporating an ultrasonic vibrator and a radio frequency source in an endoscopic surgical aspirator apparatus, the radio frequency source is cited only for coagulation. Specifically, FIG. 13, which is also disclosed in U.S. Pat. No. 4,750,902, shows elements of an alternate generator for driving the EUA in electro-cauterization of tissue. A double-pole, two-position switch 230 is provided for selecting the source of the signal to be applied to the transducer cable 130. In one position the switch selects the transducer drive signal across capacitors $C_1$, $C_2$ in the generator system. In the other position the conductor and coaxial shield of the cable 130 are tied together and connected to a radio-frequency source 232. The RF signal is advantageously a pulsed RF current with a peak amplitude of 1500 volts. The waveform is a sharply decaying damped sinusoidal waveform with a frequency of about 500 kHz. The pulse repetition rate is about 20 kHz. To complete the circuit from the RF source to ground, a grounded dispersive electrode 234 is placed in contact with the skin of the patient. The surface area of contact should be as great as possible to prevent burns and shock effects. Thus, RF provided to the tip 80 passes through the patient to ground for endoscopic tissue cauterization. The generator advantageously has the following operator controls: on/off switches for vibration, aspiration, and light; continuous/pulsed ultrasonic vibration mode; vibration amplitude; and optionally a switch 230 to connect the EUA to an RF source.

The apparatus described above can be modified so that the RF signal is able to cut as well as cauterize tissue. This can be accomplished by applying a RF signal of a particular waveform and magnitude depending on what effect is desired. The coagulating current is produced by short bursts of high frequency alternating voltage, typically lasting 10 microseconds, repeated every 50 microseconds, of as high as 3,000 volts. The cutting current is produced by a continuous wave of voltage whose magnitude is in the range of 200 to 300 volts.

Furthermore, it is possible to modify the ultrasonic generator and the radio frequency source of the endoscopic ultrasonic aspirator of U.S. Pat. No. 4,750,902 to permit independent direct connection of the RF source to the tip. Such a modification would permit the use of either ultrasonic vibration, electro-surgical current or the simultaneous application of each function.

Independent application is secured by taking advantage of the disparate frequencies employed for ultrasonic vibration and electro-surgery. Typically the ultrasonic generator produces electrical currents to power the transducer that are in the range of 20,000 Hertz. Electro-surgical generators, on the other hand, produce electrical currents in the range of 500,000 to 2 million Hertz, or more than 25 times those typical of ultrasonic surgical devices.

By installing traps or insulation to block the radio frequency current from flowing into the ultrasonic generator and the currents produced by the ultrasonic generator from flowing into the radio frequency source, removing the earthed connection of the transducer and connecting the ultrasonic feedback to an isolation transformer, both systems are prevented from interfering with each other and can be activated independently or in combination.

Figure 14:
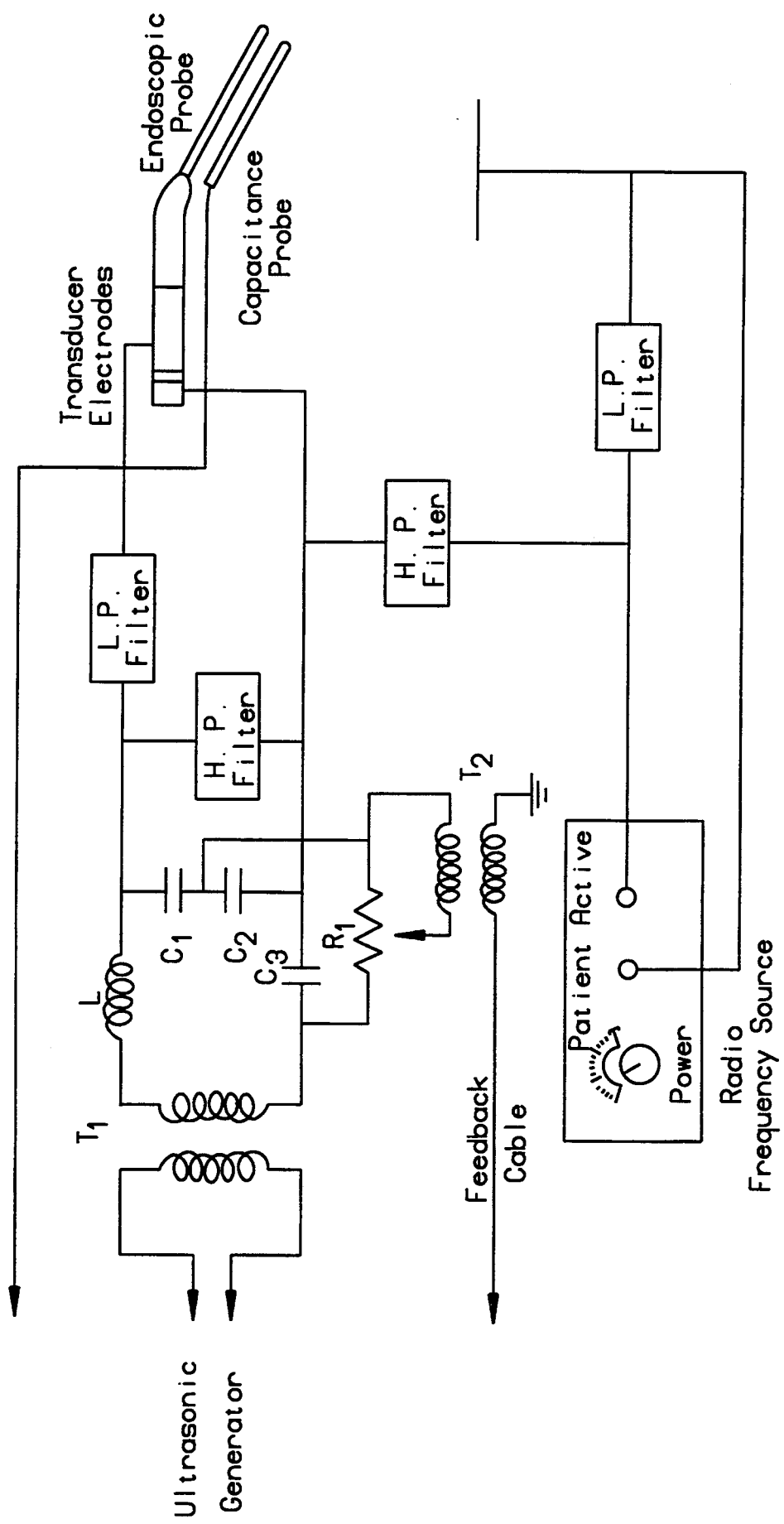
FIG. 14 is a block diagram of an ultrasonic power supply and a radio frequency power supply which can be operated independently from each other through the use of high and low pass filters.

FIG. 14 illustrates the use of these traps and transformer to provide the required isolation. This drawing modifies FIG. 10A of U.S. Pat. No. 4,750,902 and as described above. The traps consist of high and low pass filters. A high pass filter, as used here, allows radio frequency current to freely flow but blocks currents of the ultrasonic frequency. A low pass filter, as used here, allows electrical currents of the ultrasonic frequency to freely flow but blocks currents of the radio frequencies. The design of these filters is well known in electrical science. Many different methods are available for their design and construction. It is therefore sufficient for present purposes that the range of frequencies over which they discriminate be identified.

The filters shown connected to the output of the ultrasonic generator permit the flow of the ultrasonic current to the transducer but block, through the low pass filter, any current directly or capacitively coupled through transducer that is produced by the radio frequency source from entering the ultrasonic generator. The high pass filter further ensures, by acting as an electrical short circuit at radio frequencies, that any residual radio frequency current not blocked by the high pass filter does not enter the ultrasonic generator.

In a similar fashion, appropriate filters are installed on the output of the radio frequency source to ensure that ultrasonic currents do not enter the electro-surgical generator. Because the electro-surgical currents are collected at the indifferent electrode, identified usually as the patient electrode whose potential is kept close to the earth, the earthed return shown in U.S. Pat. No. 4,750,902 for the transducer drive in FIG. 10A has been removed. The earth referenced feedback signal required by the ultrasonic generator is reestablished using the isolation transformer shown.

Another embodiment of the present invention is an endoscopic surgical aspirator which exclusively uses a radio frequency generator to cut and cauterize tissue whereby the electrical potential is applied directly to the tip of the probe. This may be conveniently accomplished by using the same components as described for the endoscopic ultrasonic aspirator of U.S. Pat. No. 4,750,902, and as described above. An aspirator system is preferably used in conjunction with this exclusively electro-surgical apparatus to facilitate surgery and biopsy. The use of an electro-surgical apparatus without an aspirator system is known to those skilled in the art and is documented in the literature (e.g., Therapeutic Medical Devices-Application and Design edited by Albert M. Cook and John G. Webster, Prentice-Hall, 1982, Chap. 10). None of these systems contemplated the use of aspiration.

In this embodiment, the fluid used to irrigate the work site should be non-conductive. Examples of such non-conductive solutions include isotonic glycine, a solution of dextran or polyvinyl pyrrolidone. For certain procedures, an inert gas such as $CO_2$, nitrogen or the like can be used. When gas is used as the fluid medium, care should be taken to assure that the gas does not enter the surrounding tissue or introduce undesirable contaminants, such as oxygen into the vascular system of the patient, in order to avoid complications. The use of such non-conductive fluids would also be desirable for situations when the electrical generating system is used solely to cauterize tissue. The invention also contemplates the use of a laser for fulguration of tissue. Typically, a Nd:YAG source 100, as shown in FIG. 15 can be utilized to generate a laser beam which directed to the work site through a fiber optic element 128, and into the viewing means. This fiber optic element 128 may also be directed through one of the hollow bores or is otherwise placed within the outer sheath. This element can be mounted at the forward tip of the unit or at any appropriate position where it can be directed and "aimed" at the unwanted tissue for removal thereof. The laser provides an advantage in that it destroys unwanted tissue while simultaneously stops bleeding of adjacent tissue. However, if desired, the ultrasonic vibration generating beams and/or the RF current generating means can be used in combination with the laser for certain critical applications.

While it is apparent that the invention herein disclosed is well calculated to fulfill the object above stated, it will be appreciated that numerous modifications and embodiments may be devised by those skilled in the art, and it is intended that the appended claims cover all such modification and embodiments as fall within the true spirit and scope of the present invention.

I claim:

1. An endoscopic electrosurgical apparatus for removal of unwanted biological material through a naturally occurring or surgically created opening in the body of a patient comprising:

a handpiece;

an elongated sheath extending from said handpiece, said elongated sheath having a distal end and having a hollow bore therethrough;

a resonator assembly disposed within the handpiece and elongated sheath, said resonator assembly including an elongated tool having a tip extending beyond the distal end of the elongated sheath to a work site in the body of a patient;

means mounted in said handpiece for generating electrical energy and for transmitting said electrical energy to said resonator assembly in an amount sufficient to enable said tip of the elongated tool to disintegrate unwanted biological material from the patient or to cauterize tissue of the patient at said work site;

means mounted in said handpiece for generating ultrasonic vibrations and for transmitting said vibrations to said resonator assembly to enable said tip of the elongated tool to vibrate to incise unwanted biological material from the patient at said work site;

means for irrigating said work site with fluid to assist in removal of disintegrated biological material;

aspiration means for removing said disintegrated biological material from said work site through said elongated sheath; and means for viewing said work site from said handpiece.

2. The apparatus of claim 1 wherein the means for generating electrical energy comprises a radio frequency generator.

3. The apparatus of claim 2 wherein the means for generating electrical energy provides a continuous current from 200 to 200 volts.

4. The apparatus of claim 2 wherein the means for generating electrical energy provides short bursts of high frequency alternating voltage of ten microseconds, repeated every 50 microseconds, of as high as 3,000 volts.

5. An endoscopic electrosurgical apparatus for removal of unwanted biological material through a naturally occurring or surgically created opening in the body of a patient comprising:

a handpiece;

an elongated sheath extending from said handpiece, said elongated sheath having a distal end and having a hollow bore therethrough;

a resonator assembly disposed within the handpiece and elongated sheath, said resonator assembly including an elongated tool having a tip extending beyond the distal end of the elongated sheath to a work site in the body of a patient;

means mounted in said handpiece for generating electrical energy and for transmitting said electrical energy to said resonator assembly, in combination with means mounted in the handpiece for generating ultrasonic vibrations and for transmitting said vibrations to said resonator assembly to enable said tip of the elongated tool to vibrate to incise unwanted biological material from the patient at said work site;

means extending through said elongated sheath for irrigating said work site with fluid to assist in removal of disintegrated biological material;

aspiration means for removing said disintegrated biological material from said work site through said elongated sheath; and means extending through said elongated sheath for viewing said work site from said handpiece.

6. The apparatus of claim 5 which further comprises means for operating the electrical energy generating means in a manner to cauterize tissue.

7. The apparatus of claim 5 wherein the vibration generating means and the electrical energy means are isolated from each other by use of high pass filters to block electrical currents of low frequency produced by the vibration generator from flowing into the electrical energy source and use of low pass filters to block electrical currents of high frequency produced by the electrical energy source from flowing into the ultrasonic generator.

8. The apparatus of claim 5 wherein the resonator assembly includes:
(a) a first portion including a high frequency vibration source;
(b) a second portion comprising:
first velocity transformer means, located in the hollow bore within the sheath and spaced therefrom, for amplifying vibrations from the vibration source and having an input section and an output section, the input section being unitary with the vibration source and the output section being smaller in cross-sectional area than the input section, and
second velocity transformer means having an input end and an output end, the input end being unitary with the output section of the first velocity transformer means, for amplifying vibrations thereof to a sufficient velocity to disintegrate such unwanted biological material and to minimize production of transverse flexural vibrations, the output end vibrating in response to such received vibrational energy for further transmitting such vibrational energy; and
(c) a third portion comprising the elongated tool means coupled to the output end of said second velocity transformer means and passing through the hollow bore of the sheath to said work site beyond the distal end of the sheath for transmitting amplified vibrations to said work site for removal of portions of biological material thereof.

9. The surgical apparatus claim 5 wherein said means for irrigating the work site includes a fluid passage defined between said transformers and said sheath, and said apparatus further comprises fluid detection means for detecting the presence of fluid in the fluid passage and being connected to means for supplying alternating current to the vibration generating means for terminating such supplied alternating current and thereby stopping the vibration generating means from generating mechanical vibrations when such fluid is not present in the fluid passage.

10. The apparatus of claim 10 wherein the fluid detection means includes electrical means coupled to the fluid passage for sensing the electrical capacitance in the fluid passage and terminating such supplied alternating current when the capacitance is above a predetermined level to indicate that fluid is not present.

11. The apparatus of claim 10 wherein said electrical means includes a conductive probe, and said capacitance is measured between said probe and said energy or vibration generating means.

12. The apparatus of claim 11, wherein said probe is located within the sheath and runs substantially parallel with the energy or vibration generating means.

13. The apparatus of claim 12 wherein the viewing means extends through a second bore in the sheath that is not exposed to fluid from said fluid passage; and the probe is located within said second bore.

14. An endoscopic electrosurgical apparatus for the removal of unwanted biological material through a natural occurring or surgically created opening in the body of a patient comprising:
a handpiece;
an elongated sheath extending from said handpiece, said elongated sheath having a distal end and having a hollow bore therethrough;
a resonator assembly disposed within the handpiece and elongated sheath, said resonator assembly including an elongated tool having a tip extending beyond the distal end of the elongated sheath to a work site in the body of a patient;
laser means extending through said elongated sheath to beyond the distal end thereof for fulgurating unwanted biological material with laser energy from the patient at said work site;
means mounted in said handpiece for generating ultrasonic vibrations and for transmitting said vibrations to said tip of the resonator to enable said elongated tool to vibrate to incise unwanted biological material from the patient at said work site;
means for irrigating said work site with fluid to assist in removal of disintegrated biological material;
aspiration means for removing said disintegrated biological material from said work site through said elongated sheath; and
means extending through said elongated sheath for viewing said work site from said handpiece.

15. The apparatus of claim 14 wherein the laser means comprises a Nd:YAG laser source and a fiber optic element which extends from said source through said bore to the work site.

16. The apparatus of claim 14 wherein the laser means comprises a Nd:YAG laser source and a fiber optic element which extends from said source within said sheath to the work site.

17. The apparatus of claim 14 further comprising electrical fluid detection means for detecting fluid in a fluid space located in the sheath, said fluid detection means connected to means for supplying alternating current to the means for generating ultrasonic vibrations for terminating such supplied alternating current and thereby stopping such ultrasonic vibrations when such fluid is not present.

18. The apparatus of claim 14 further comprising means for generating electrical energy.

19. The apparatus of claim 18 wherein the resonator assembly comprises:
(a) a first portion including a high frequency vibration source;
(b) a second portion comprising:
first velocity transformer means located in the hollow bore within the sheath and spaced therefrom for amplifying vibrations from the vibration source and having an input section and an output section, the input section being unitary with the vibration source means and the output section being smaller in cross-sectional area than the input section, and
second velocity transformer means having an input end and an output end, the input end being unitary with the output section of the first velocity transformer means for amplifying vibrations thereof to a sufficient velocity to disintegrate such unwanted biological material and to minimize the production of transverse flexural vibrations, the output end vibrating in response to such received vibrational energy for further transmitting such vibrational energy; and
(c) a third portion comprising the elongated tool means coupled to the output end of said second velocity transformer means and passing through the hollow bore of the sheath to said work site beyond the distal end of the sheath for transmitting the amplified vibrations to said work site for removal of portions of biological material thereof.

20. The apparatus of claim 1, 5 or 14 wherein the circumference of the elongated sheath is not greater than 29 mm.

21. The apparatus of claim 1 or 5 wherein the fluid introduced for irrigating the work site is electrically non-conductive.

22. The apparatus of claim 21 wherein said fluid is one of isotonic glycine, a dextran solution, polyvinyl pyrolidone, or a gas.

23. The apparatus of claim 1, 5 or 14 wherein the means for irrigating the work site comprises
  (a) means for introducing fluid into one fluid passage means along the bore of said sheath; and
  (b) means for applying suction to another fluid passage means along the bore of said sheath 24. The apparatus of claim 23 wherein said means for applying suction to said other fluid passage includes
  (a) hose means for receiving such fluid and tissue,
  (b) biopsy valve means coupled to said hose means for selectively diverting fluid and tissue out of said hose means
  (c) biopsy trap means for receiving such fluid and tissue selectively diverted out of said hose means to filter selected tissue therefrom, and
  (d) pump means for applying suction force to said biopsy trap means and to said hose means.

25. The apparatus of claim 23 wherein the hose means includes a length of hose less than 0.5 meter long connected both to the biopsy valve means and to said fluid passage to which suction is applied.

26. The apparatus of claim 23 further comprising aspiration trap means for collecting tissue that is not selectively diverted out of the hose means.

* * * * *